United States Patent [19]
Lee

[11] Patent Number: 5,582,166
[45] Date of Patent: Dec. 10, 1996

[54] DEVICE TO FACILITATE SECURING AN ENDOTRACHEAL TUBE TO AN ADAPTOR CONNECTED TO A SUCTION OR GAS SOURCE

[76] Inventor: Cindy Lee, 9120 Hoffman Farm La., Cincinnati, Ohio 45242

[21] Appl. No.: 558,659

[22] Filed: Nov. 16, 1995

[51] Int. Cl.⁶ .................................................. A61M 16/00
[52] U.S. Cl. ................ 128/207.14; 128/202.27; 128/912; 128/DIG. 26
[58] Field of Search ............ 128/202.27, 207.17, 128/912, DIG. 26, 207.14, 207.15; 24/135 A, 135 R, 136 B; 285/245, 249, 250

[56] References Cited

U.S. PATENT DOCUMENTS

| | | | |
|---|---|---|---|
| 36,410 | 9/1862 | Jucket | 285/245 |
| 1,506,048 | 8/1924 | Charette | 285/250 |
| 2,694,584 | 11/1954 | Miller | 285/250 |
| 3,923,323 | 12/1975 | Brogan | 285/250 |
| 4,304,228 | 12/1981 | Depel | 128/207.17 |
| 4,332,245 | 6/1982 | Boone, Sr. | 128/207.17 |
| 5,146,913 | 9/1992 | Khorsandian et al. | 128/912 |
| 5,176,415 | 1/1993 | Choksi | 128/202.27 |
| 5,251,616 | 10/1993 | Desch | 128/912 |

*Primary Examiner*—Aaron J. Lewis
*Attorney, Agent, or Firm*—Wood, Herron & Evans, P.L.L.

[57] ABSTRACT

A device to facilitate securing an endotracheal tube to an adaptor connected to a suction or gas source is disclosed. The device is comprised of a collar slidable over an endotracheal tube and adaptor. The collar has a prong for engaging the endotracheal tube. The device is further comprised of a ring for temporarily locking to the collar and forcing the collar prong into fastening engagement with the tube.

16 Claims, 1 Drawing Sheet

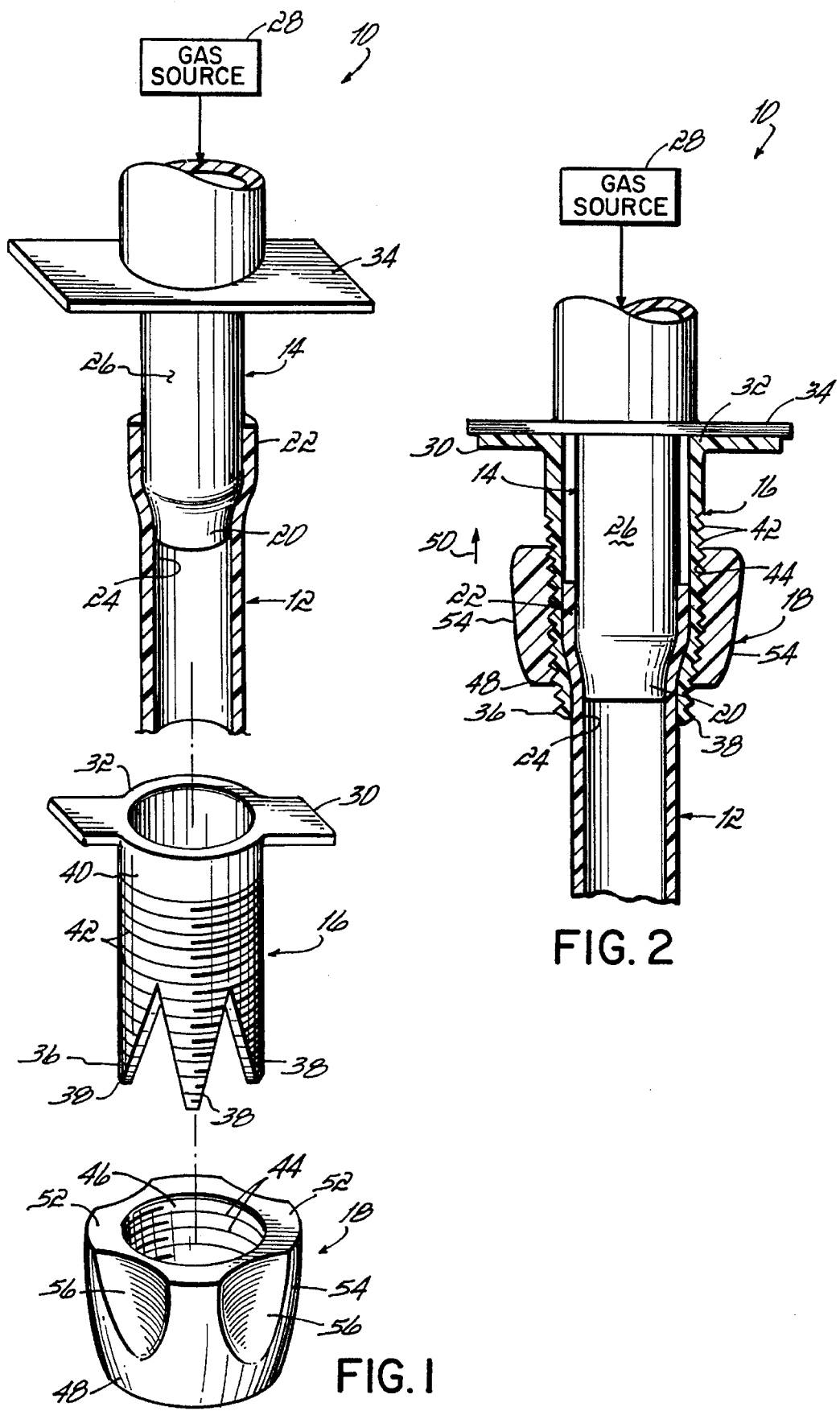

5,582,166

DEVICE TO FACILITATE SECURING AN ENDOTRACHEAL TUBE TO AN ADAPTOR CONNECTED TO A SUCTION OR GAS SOURCE

FIELD OF THE INVENTION

This invention generally relates to a device that facilitates securing an endotracheal tube to an adaptor connected to a gas or suction source to prevent the disjunction of the source from the tube.

BACKGROUND OF THE INVENTION

During various medical procedures, it is often necessary to insert an endotracheal tube into a patient for such purposes as administering anesthesia. Generally, the prior art tube is connected to an endotracheal tube adaptor, which in turn, is connected to a gas source. Typically, the adaptor has a tubular first end that slides partially in a first end of the endotracheal tube to form a telescoping connection (more commonly known as a male-female connection) therebetween. The adaptor has a second end portion adapted to receive and secure a gas source. A danger exists that the endotracheal tube and adaptor will become disconnected as the tubular first end of the adaptor can easily slide out of the first end of the tube. For example, if such disconnection occurs while the tube is in a patient, the source will in turn become disconnected from the patient resulting in the interruption of oxygen and/or anesthesia and the possibility of harm to the patient. In other instances when the endotracheal tube is used for suctioning or lavaging the lungs, such an interruption can be threatening to the well being of the patient. Also, when the tube becomes disconnected from the adaptor, the adaptor often becomes lost as it may fall on the floor or on the operating table thereby making it impossible to reconnect the source to the patient.

Accordingly, it is a primary objective of this invention to provide a device that facilitates securely joining an endotracheal tube to an adaptor connected to a source without the risk of the source becoming disconnected while the tube is within a patient.

BRIEF SUMMARY OF THE INVENTION

This invention provides a device that facilitates securing an endotracheal tube to a first end of an adaptor slidably receivable in a first end of the endotracheal tube. The second end of the adaptor is connected to a suction or gas source. The device is comprised of a collar that is slidable over the endotracheal tube and the adaptor. A first end of the collar is positioned around the adaptor while a second end of the collar is positioned around the endotracheal tube. The end of the collar positioned around the endotracheal tube has a prong for engaging the endotracheal tube. A ring is received over the collar and has a locking means for temporarily locking the ring to the collar and for forcing the collar prong into fastening engagement with the tube.

In a preferred form, the ring has a threaded interior surface while the collar has a threaded exterior surface for cooperative engagement with one another. More specifically, the ring may be screwed to the collar thereby temporarily locking the ring to the collar which preferably has a plurality of prongs. The ring may be tapered so that when the ring moves up the collar upon screwing the ring to the collar, the tapered end pushes the prongs of the collar inward thereby sandwiching the endotracheal tube between the prongs of the collar and the adaptor.

In other subsidiary aspects of the invention, the ring may have a flange or a plurality of flanges extending generally perpendicularly from an exterior surface of the ring to facilitate grasping and twisting of the connector. The collar, including the collar prongs, may be flexible and comprised accordingly of plastic.

BRIEF DESCRIPTION OF THE DRAWINGS

FIG. 1 is disassembled perspective view of the endotracheal system employing the device of the present invention.

FIG. 2 is a partial cross sectional view of the device of FIG. 1.

DETAILED DESCRIPTION OF THE PREFERRED EMBODIMENT

With reference to FIGS. 1 and 2, an endotracheal system 10 is provided and comprised of an endotracheal tube 12 and an endotracheal tube adaptor 14. Additionally, system 10 is comprised of a collar 16 and a ring 18.

A first end 20 of adaptor 14 is slidably receivable in a first end 22 of tube 12 to form a telescoping connection, more commonly known as a male-female connection. First end 20 of adaptor 14 is held in position by friction between the inner surface 24 of tube 12 and the outer surface 26 of adaptor 14. Although tube 12 and adaptor 14 are held in position by friction, it is fairly simple for tube 12 and adaptor 14 to slide apart and become completely disengaged during a medical procedure. Often, the adaptor 14 falls onto the ground or onto the operating table (not shown) when disengagement occurs and cannot be found, making reengagement of adaptor 14 and tube 12 impossible. Disengagement of tube 12 and adaptor 14 is dangerous since adaptor 14 is in turn, typically connected to the patient's gas or anesthesia source 28. Thus, if tube 12 and adaptor 14 become disconnected from one another, oxygen and/or anesthesia will, in turn, become disconnected from the patient. Similarly, if tube 12 is being used to suction the lungs of a patient and becomes disconnected from adaptor 14, the well being of the patient will be at risk. It is therefore critical that source 28 not become disconnected from system 10 while endotracheal tube 12 is within the trachea of the patient.

Collar 16 and ring 18 prevent such disengagement of endotracheal tube 12 from adaptor 14 and source 28. Collar 16 is adapted to slide over tube 12 and adaptor 14. Collar 16 has a winged member 30 at a first end 32 of collar 16 that succinctly abuts winged member 34 of adaptor 14. Second end 36 of collar 16 is pronged, generally having at least two and preferably three or more prongs 38. Additionally, collar 16 is threaded on its exterior surface 40 as shown by threads 42 particularly in FIG. 2.

Once collar 16 is positioned around adaptor 14 and tube 12, ring 18 can be assembled with system 10. Ring 18 has threads 44 on its interior surface 46. Additionally, ring 18 is advantageously tapered. Ring 18 is slid over tube 12 and engages with collar 16. Threads 44 of ring 18 cooperatively engage with threads 42 of collar 16 such that ring 18 is screwed onto collar 16 like a nut being screwed onto a bolt. Ring 18, however, is tapered to prevent ring 18 from being screwed completely up collar 16. As ring 18 engages with collar 16 via threads 42, 44, tapered end 48 of ring 18 pushes prongs 38 of collar 16 inward against tube 12. Tube 12 thus becomes sandwiched between prongs 38 of collar 16 and first end 20 of adaptor 14 located within first end 22 of tube 12. As ring 18 is screwed upward as in direction of arrow 50 around collar 16, prongs 38 are pushed more tightly against tube 12 such that it becomes impossible for tube 12 to disconnect from adaptor 14. Thus, the risk of source 28 becoming disconnected from system 10 is significantly reduced, if not eliminated.

To facilitate securing ring 18 to collar 16, flanges 52 are located around the exterior surface 54 of ring 18. Flanges 52 extend generally perpendicularly from exterior surface 54 of ring 18 to provide a user with an effective manner of grasping and twisting ring 18 for threading onto collar 16. Additionally, finger depressions 56 may be located on the exterior surface 54 of ring 18 to further facilitate grasping and twisting of ring 18.

Based on the foregoing description, it will be appreciated that the collar 16 and ring 18 of the present invention provide the ability to easily and securely connect a source 28 to an endotracheal tube 12 via an adaptor 14. It is quick and easy to screw the ring 18 to the collar 16 thereby securing the tube 12 to the adaptor 14 and source 28. As it is quick and easy to screw the ring 18 to the collar 16, it is just as easy to unscrew the ring 18 from the collar 16 to disconnect the tube 12 from the adaptor 14 and source 28.

From the above description of the general principles of the present invention and the preceding detailed description of a preferred embodiment, those skilled in the art will readily comprehend the various modifications to which the present invention is susceptible without departing from the scope of the present invention.

What is claimed is:

1. An endotracheal tube, an adaptor, and a device to facilitate securing the endotracheal tube to a first end of the adaptor slidably positioned in a first end of said endotracheal tube, and the adaptor connectable at a second end to a suction or gas source, comprising:

a collar slidably positioned over said endotracheal tube and said adaptor, a first end of said collar being positioned around said adaptor and a second end of said collar is positioned around said endotracheal tube, said second end of said collar having at least one prong for engaging said endotracheal tube; and a ring removably position over said collar, said ring having locking means for temporarily locking said ring to said collar and forcing said collar prong into fastening engagement with said endotracheal tube.

2. The device of claim 1 wherein said ring has a threaded locking means for temporarily locking said collar to said ring.

3. The device of claim 2 wherein said collar has a threaded exterior surface for cooperative engagement with said threaded ring.

4. The device of claim 1 wherein said ring is tapered.

5. The device of claim 1 wherein said ring has a flange extending generally perpendicularly from an exterior surface of said ring to facilitate grasping and twisting of said ring.

6. An endotracheal tube, an adaptor, and a device to facilitate securing the endotracheal tube to a first end of the adaptor slidably positioned in a first end of said endotracheal tube, and the adaptor connectable at a second end to a suction or gas source, comprising:

a collar slidably positioned over said endotracheal tube and said adaptor, a first end of said collar being positioned around said adaptor and a second end of said collar being positioned around said endotracheal tube, said second end of said collar having at least one flexible prong for engaging said endotracheal tube; and a ring having locking means for temporarily locking said ring to said collar and for forcing said collar prong inward thereby sandwiching said endotracheal tube between said collar prong and said adaptor.

7. The device of claim 6 wherein said ring has a threaded locking means for temporarily locking said collar to said ring.

8. The device of claim 7 wherein said collar has a threaded exterior surface for cooperative engagement with said threaded ring.

9. The device of claim 6 wherein said ring is tapered.

10. The device of claim 6 wherein said ring has a flange extending generally perpendicularly from an exterior surface of said ring to facilitate grasping and twisting of said ring.

11. An endotracheal tube, an adaptor, and a device to facilitate securing the endotracheal tube to a first end of the adaptor slidably positioned in a first end of said endotracheal tube, and the adaptor connectable at a second end to a suction or gas source, comprising:

a plastic collar slidably positioned over said endotracheal tube and said adaptor, a first end of said collar being positioned around said adaptor and a second end of said collar being positioned around said endotracheal tube, said second end of said collar having a plurality of flexible prongs for engaging said endotracheal tube; and a plastic ring having locking means for temporarily locking said ring to said collar and for forcing said collar prongs inward thereby sandwiching said endotracheal tube between said collar prongs and said adaptor.

12. The device of claim 11 wherein said ring and collar have a threaded locking means for temporarily locking said collar to said ring.

13. The device of claim 11 wherein said ring is tapered.

14. The device of claim 11 wherein said ring has a flange extending generally perpendicularly from an exterior surface of said ring to facilitate grasping and twisting of said ring.

15. The device of claim 12 wherein said collar prongs have a threaded exterior surface for locking the collar to the ring.

16. The device of claims 1,6 and 11 wherein the first end of said collar has a winged member extending generally perpendicularly from an exterior surface of said collar for securement against said adaptor.

* * * * *